(12) United States Patent
Mirsiaghi et al.

(10) Patent No.: US 10,907,223 B2
(45) Date of Patent: Feb. 2, 2021

(54) METHOD TO PRODUCE A POLYSACCHARIDE GEL BY INCREASING THE PH OF THE POLYSACCHARIDE

(71) Applicants: The Regents of the University of California, Oakland, CA (US); HelioBioSys, Inc., Woodside, CA (US)

(72) Inventors: Mona Mirsiaghi, Emeryville, CA (US); Eric Sundstrom, San Mateo, CA (US); Deepti Tanjore, Emeryville, CA (US); Todd Pray, Millbrae, CA (US); Rocco L. Mancinelli, Woodside, CA (US); David T. Smernoff, Portola Valley, CA (US)

(73) Assignees: The Regents of the University of California, Oakland, CA (US); HelioBioSys, Inc., Woodside, CA (US)

( * ) Notice: Subject to any disclaimer, the term of this patent is extended or adjusted under 35 U.S.C. 154(b) by 0 days.

(21) Appl. No.: 15/943,597

(22) Filed: Apr. 2, 2018

(65) Prior Publication Data
US 2018/0282826 A1    Oct. 4, 2018

Related U.S. Application Data

(60) Provisional application No. 62/480,117, filed on Mar. 31, 2017.

(51) Int. Cl.
| | |
|---|---|
| *C12N 1/20* | (2006.01) |
| *C12P 19/04* | (2006.01) |
| *C08B 37/00* | (2006.01) |
| *C12R 1/01* | (2006.01) |

(52) U.S. Cl.
CPC ............ *C12R 1/01* (2013.01); *C08B 37/0057* (2013.01); *C12P 19/04* (2013.01); *C12N 1/20* (2013.01)

(58) Field of Classification Search
None
See application file for complete search history.

(56) References Cited

U.S. PATENT DOCUMENTS

| | | | |
|---|---|---|---|
| 2009/0137013 A1* | 5/2009 | Schmid | C12P 7/6463 435/134 |
| 2013/0183732 A1* | 7/2013 | Mancinelli | C12N 1/16 435/162 |
| 2015/0099878 A1* | 4/2015 | Logas Gonzalez | C07D 473/00 544/251 |

OTHER PUBLICATIONS

Wu et al. Carbohydr Polym. Oct. 1, 2017;173:465-472 (Year: 2017).*
Haroyo et al., "Physicochemical Properties and the Gelation Process of Supramolecular Hydrogels: A Review", Gel, 3(1): 1, 2017 (18 pages).
Wu et al., "Separation of Polysaccharides from Spirulina platensis by HSCCC with ethanol-ammonium solfate ATPS and theri antioxidant activities", vol. 173, pp. 165-472, 2017.

* cited by examiner

*Primary Examiner* — Christian L Fronda
(74) *Attorney, Agent, or Firm* — Robin C. Chiang; Lawrence Berkeley National Laboratory

(57) ABSTRACT

The present invention provides for a method of producing a polysaccharide gel comprising: (a) culturing or growing a cyanobacterium or a mixture of cyanobacteria species in a medium under conditions such that the cyanobacterium or the mixture of cyanobacteria species produces a polysaccharide or a mixture of polysaccharides, (b) optionally separating the polysaccharide or the mixture of polysaccharides from the medium and/or the cyanobacterium or the mixture of cyanobacteria species, and (c) increasing the pH of the polysaccharide or the mixture of polysaccharides such that the polysaccharide or the mixture of polysaccharides forms a gel.

5 Claims, 2 Drawing Sheets

METHOD TO PRODUCE A POLYSACCHARIDE GEL BY INCREASING THE PH OF THE POLYSACCHARIDE

RELATED PATENT APPLICATIONS

The application claims priority to U.S. Provisional Patent Application Ser. No. 62/480,117, filed Mar. 31, 2017, which is herein incorporated by reference in its entirety.

STATEMENT OF GOVERNMENTAL SUPPORT

The invention was made with government support under Contract No. DE-AC02-05CH11231 awarded by the U.S. Department of Energy. The government has certain rights in the invention.

FIELD OF THE INVENTION

The present invention is in the field of polysaccharides.

BACKGROUND OF THE INVENTION

Existing commercialized bacterial exopolysaccharides include xanthan and gellan—both of these products are heavily used in the food industry with xanthan production exceeding 20,000 tons/year. Xanthan and gellan are typically used as thickeners for foods and cosmetics. Other gel-forming polysaccharides include chitosan, gelatin, and agarose. Both gelatin and chitosan are derived from animal products, creating a significant market for non-animal derived alternatives. In addition to use as food thickeners, these materials are used for gel electrophoresis, for drug delivery, for encapsulation of cells and resins, as flocculants, and as biomaterials. Certain polysaccharides, including chitosan, form gels at low pH, but there are no documented reports of polysaccharides (including commercial and non-commercial materials) that remain in solution at low and neutral pH with spontaneous gel formation at high pH.

SUMMARY OF THE INVENTION

The present invention provides for a method of producing a polysaccharide gel comprising: (a) culturing or growing a cyanobacterium or a mixture of cyanobacteria species in a medium under conditions such that the cyanobacterium or the mixture of cyanobacteria species produces a polysaccharide or a mixture of polysaccharides, (b) optionally separating the polysaccharide or the mixture of polysaccharides from the medium and/or the cyanobacterium or the mixture of cyanobacteria species, and (c) increasing the pH of the polysaccharide or the mixture of polysaccharides such that the polysaccharide or the mixture of polysaccharides forms a gel. In some embodiments, the increasing the pH step comprises increasing the pH to a value equal to or more than pH 9.0, pH 9.5, pH 10.0, pH 10.5, pH 11.0, or pH 11.5.

The present invention provides for a composition comprising a polysaccharide gel produced by the method of this present invention. In some embodiments, the polysaccharide gel has a viscosity with a value from about 1000 to about 5000 Pa·s in a stress sweep from about 1 to about 10 Pa.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
FIG. 1 shows concentrated polysaccharide after ethanol addition and mixing. Polysaccharide is visible as a cloudy suspension.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

As used in the specification and the appended claims, the singular forms "a", "an", and "the" include plural references unless the context clearly dictates otherwise. Thus, for example, reference to a "polysaccharide" includes a single polysaccharide molecule, and a plurality of polysaccharide molecules having the same, or similar, chemical formula, chemical and/or physical properties.

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

These and other objects, advantages, and features of the invention will become apparent to those persons skilled in the art upon reading the details of the invention as more fully described below.

In some embodiments, the increasing the pH step comprises introducing a base to the polysaccharide or the mixture of polysaccharides. In some embodiments, the base is a hydroxide solution, such as an alkali metal hydroxide, such as sodium hydroxide or potassium hydroxide, or an ammonium hydroxide, or a mixture thereof.

In some embodiments, the base is a monovalent base or a divalent base, or a mixture thereof. In some embodiments, the monovalent base is ammonium hydroxide, sodium hydroxide or potassium hydroxide, or a mixture thereof. In some embodiments, the divalent base is calcium hydroxide.

In some embodiments, the polysaccharides are cyanobacterial polysaccharides. In some embodiments, the polysaccharides are further deconstructed, hydrolyzed, or fermented to obtain monosaccharides, and optionally the monosaccharides are as a carbon source for microbes to produce a product, such as a biofuel. In some embodiments, the separating step comprises one or more of the following steps: separating the polysaccharide from the cyanobacterial cells by centrifugation, removing salts via membrane filtration and diafiltration, concentrating the polysaccharide in the slurry via tangential flow filtration, and precipitating the purified polysaccharides in ethanol. In some embodiments, the polysaccharide, or a part thereof, is hydrolyzed into individual monosaccharides.

The resulting monosaccharides can be analyzed via High Pressure Liquid Chromatography. The resulting hydrolysate can be fermented to produce a biofuel. Prior to fermentation, when adjusting pH of the slurry to 7, increasing gel-like behavior is observed in samples that were not fully hydrolyzed. When the pH is further increased, the gel-like behavior increased, and consistent substantial gel-formation is observed at pH equal to or more than 10.5.

In some embodiments, the separating step comprises the polysaccharides in a two-step process of centrifugation and pH adjustment. These steps are significantly cheaper than existing documented protocols and alternatives, which include precipitation with ethanol, and the like.

In some embodiments, gels are produced from a cyanobacterial slurry comprising equal to or more than about 1% solids concentration. In some embodiments, the slurry comprises: (i) a raw culture, with cells and polysaccharides, (ii) a centrifuged culture with cells separated and removed from extracellular polysaccharides, (iii) a centrifuged, desalted, and concentrated polysaccharide slurry, or (iv) a centrifuged, desalted, concentrated, and hydrolyzed polysaccharide slurry. When the pH is adjusted for each of the slurries from 7 to 10.5 with 2 M sodium hydroxide and 20% (v/v) ammonium hydroxide, all of them formed gels with viscosities varying from 1000 to 5000 Pa·s in a stress sweep from 1 to 10 Pa.

Gel formation only at pH >10.5 is a novel property of these polysaccharides that has not been documented in the literature for known polysaccharides. This property has applications in two key areas: 1) improved recovery of polysaccharides from saline aqueous solutions and 2) use of spontaneous, pH-triggered gel formation for encapsulation, drug delivery, coatings, and other commercial applications. Use of pH adjustment to harvest polysaccharides would streamline recovery, lowering the cost of materials for a variety of applications. Novel gel-forming properties would help differentiate these polysaccharides from existing alternatives and would potentially open new avenues for commercialization.

Gel formation catalyzed by shifts in pH has a number of potential industrial applications. Adjusting pH, followed by centrifugation, would enable streamlined separation and purification of polysaccharides from the cyanobacterial cultivation medium. Separating polysaccharides from the saltwater cultivation medium is likely the greatest contributor to polysaccharide production cost due to the high concentration of salt (~3% w/w) in comparison to the concentration of suspended polysaccharides secreted by the cyanobacterial cultures (<0.1% w/w). In previous scale-up experiements this separation was achieved via tangential flow filtration and diafiltration with a freshwater buffer to flush salts from the system. This step was followed by ethanol precipitation. Because sea salt does not precipitate at high pH, use of gel forming properties to remove polymer directly from the cultivation medium would significantly reduce the cost and energy requirements for this separation process.

Reducing the product recovery cost would overcome a major scale-up hurdle and open additional markets for commercialization. These polysaccharides have use as a biomaterial and as gums for use in the food and cosmetics industries. Spontaneous gel formation enables other uses, for example, the self-aggregating properties of this material would be useful for flocculation and clarification in the food, beverage, water, and wastewater industries. Gel formation can also be used to encapsulate materials in a permeable gel layer, for example, this property has potential applications for drug delivery or for encapsulation of industrial microorganisms and probiotics without loss of cell viability. Spontaneous gel formation could also enable novel applications for pH-targeted drug release or for in-situ formation of gels in medical applications, or the like.

Application of the Inorganic Scintillators

The present invention provides for a gamma ray or x-ray detector, comprising: a scintillator composed of a transparent single crystal of the inorganic scintillator of the present invention, and a photodetector optically coupled to the scintillator for producing an electrical signal in response to the emission of a light pulse by the scintillator.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

EXAMPLE 1

This example describes the successful recovery, saccharification, and fermentation of polysaccharides excreted by a cyanobacterial consortium. These polysaccharides do not require fresh water or arable land for production and have potential applications as fermentable sugar, as bio-based plastics, and as thickeners and gels. Two scalable recovery processes were developed: recovery via membrane separation and diafiltration and recovery via base-catalyzed gel formation. Characterization of the polysaccharides excreted by the cyanobacterial consortium reveals a mixture of 5- and 6-carbon sugars including significant fractions of glucose, xylose, arabinose, galactose, and mannose. Fermentation baselining with *Rhodosporidium toruloides* reveals performance indistinguishable from a pure glucose control condition.

A. Process Development for Recovery and Saccharification of Polysaccharides.

Figure 2:
FIG. 2 shows concentrated polysaccharide after pelleted precipitate after centrifugation. Polysaccharide is visible as a cloudy suspension.

Concentration and recovery of polysaccharides produced by the cyanobacterial consortium is necessary to produce concentrated hydrolysates suitable for fermentation and to evaluate the intact polysaccharide for end use as a bioplastic or gel. Recovery of pure polysaccharide was achieved via a four-step process comprising: (1) centrifugation to remove cyanobacterial biomass, (2) tangential flow filtration to concentrate polysaccharides, (3) diafiltration to desalt the concentrate, and (4) ethanol precipitation to recover pure polysaccharide in solid form (FIG. 1 and FIG. 2). Initial processing was carried out using a lab scale 5 kD 0.005 $m^2$ Millipore Pellicon XL TFF membrane. Though this process may require some modification during scale-up, each of these technologies is mature and has been proven at industrial scale. The process was demonstrated with and without ethanol precipitation, which may be eliminated entirely in favor spray drying or direct hydrolysis of the concentrate following TFF. This decision will ultimately depend on the intended end use of the material.

Figure 3:
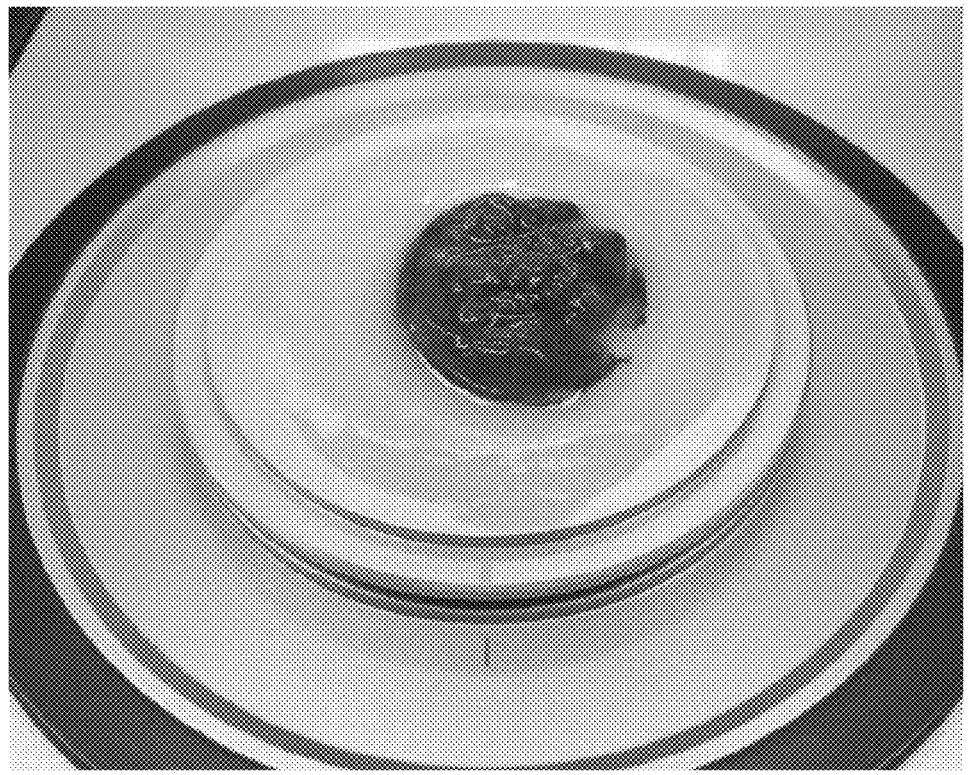
FIG. 3 shows the polysaccharide gel formed by addition of concentrated base to whole cyanobacterial culture. Gel material precipitates spontaneously with the addition of concentrated sodium hydroxide.
Figure 4:
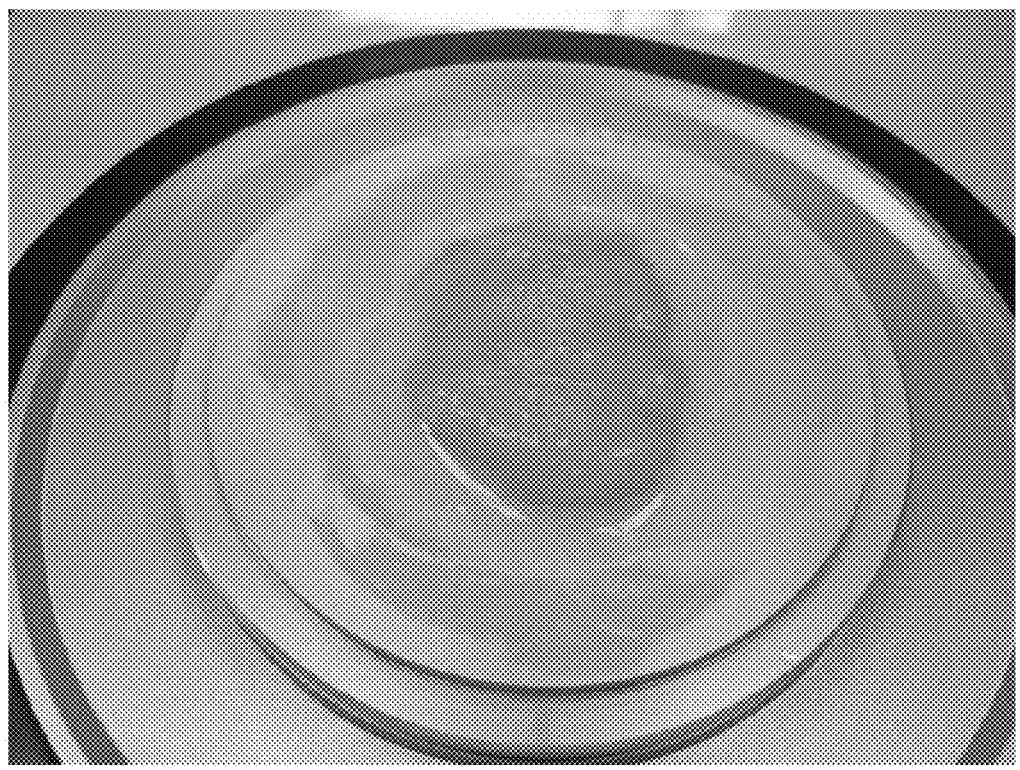
FIG. 4 shows the polysaccharide gel formed by addition of concentrated base to cyanobacterial culture supernatant. Gel material precipitates spontaneously with the addition of concentrated sodium hydroxide.

A second method for material recovery was discovered fortuitously during the scale-up phase of the research effort. While pH-adjusting the polysaccharide following dilute acid hydrolysis it became apparent that the addition of concentrated base resulted in precipitation of intact polysaccharides. Further testing revealed that sodium hydroxide addition to achieve pH>10 results in gel formation in the raw culture, culture supernatant, and concentrated polysaccharide (FIG. 3 and FIG. 4). These gel materials have a solids content of 0.1%-0.5%, much lower than for the more solid precipitates produced during ethanol precipitation (FIG. 1 and FIG. 2). This unique property has clear applications for low-cost material recovery and may enable additional downstream applications for cyanobacterial polysaccharides as thickeners in the food, cosmetics, consumer products, and chemical industries.

B. Characterization of Concentration and Composition of Biomass and Excreted Sugars.

Due to the complexity of the biomass and culture medium, total organic carbon (TOC) and chemical oxygen demand (COD) were used as proxies to quantify concentrations and losses of material during the recovery process.

testing, 37% of the total carbon remained in the supernatant during centrifugation for 15 minutes at 4700 g (Table 1). The majority of the carbon lost in this step is cyanobacterial biomass, which settles as a dense green pellet. The biomass fraction could be recovered and valorized as raw biomass for further sugar production or as high protein feed for livestock or aquaculture. Of the carbon retained in the supernatant, 75.4% was retained during tangential flow filtration with a 5 kD membrane. Carbon lost during this step likely consists of monomeric sugars, short-chain polysaccharides, and any additional short-chain molecules excreted in the cultivation stage.

A second, larger batch of material was subjected to a similar recovery process and tested via COD analysis. In this case 51% of COD remained in the culture supernatant, with 42% of the supernatant carbon retained during TFF. The second batch of material was processed soon after the end of cultivation, which may account for the higher overall organic content of the culture and the greater proportion of free sugars and short-chain polysaccharides observed.

TABLE 1

Total organic carbon and chemical oxygen demand for biomass fractions during the recovery process. Two batches of cyanobacterial culture were tested: batch 1 was characterized via TOC analysis and batch 2 was characterized via COD analysis.

| Culture | Sample | TOC (mg/L) | COD (mg/L) |
|---|---|---|---|
| 1 | Initial algae culture | 281 | — |
| 1 | Supernatant | 104 | — |
| 1 | Diafiltered concentrate (5× concentrate) | 392 | — |
| 2 | Initial algae culture | — | 1500 |
| 2 | Supernatant | — | 770 |
| 2 | TFF permeate | — | 450 |
| 2 | Diafiltered concentrate (25× concentrate) | — | 3100 |

Several hydrolysis conditions were tested on the recovered polysaccharide, including mild acid hydrolysis with acid concentrations below 0.5%. At acid concentrations below 0.5% the resulting hydrolysate was extremely viscous and not suitable for analysis via HPLC. Mild acid hydrolysis is therefore not recommended at this time, though it may be useful for inducing gel formation. Following strong acid hydrolysis, the material loses viscosity and becomes a clear liquid. Total quantified sugars topped out near 32% of the pelleted biomass; the remainder of the material is of unknown composition (Tables 2 and 3). Analysis of the remainder of the material will require more advanced carbohydrate analysis capable of analyzing additional monomers and hydrolysis byproducts.

TABLE 2

Recovery of monomeric sugars from hydrolyzed, dry pellet expressed as sugar concentration in the original culture. TOC recovery values are based on the TOC concentration following tangential flow filtration; this recovery percentage does not include any losses during centrifugation and TFF.

| Hydrolysis condition | Glu (mg/L) | Xyl (mg/L) | Gal (mg/L) | Ara (mg/L) | Man (mg/L) | Total (mg/L) | TOC (mg/L) | TOC recovery |
|---|---|---|---|---|---|---|---|---|
| 3% H2SO4 | 12.9 | 15.9 | 15.8 | 16.3 | 9.5 | 70.3 | 28.1 | 35.9% |
| 1.5% H2SO4 | 12.9 | 20.7 | 8.7 | 19.5 | 6.4 | 68.3 | 27.3 | 34.9% |
| 0.5% H2SO4 | 8.7 | 13.7 | 5.0 | 14.4 | 3.6 | 45.4 | 18.2 | 23.2% |

These analyses reveal the maximum loss during each processing step, but cannot reveal what percentage of lost carbon consists of polysaccharide material. During initial After accounting for the carbon percentage of the identified sugars, recovery of TOC as a fraction of carbon in the concentrate following TFF topped out near 36% (Table 3).

Recovery as a function of TOC was similar to recovery as a percentage of pellet weight. Identification of the remaining 60-70% of material may help close the mass balance and bring both values close to 100%. In particular, elemental analysis of the pelleted material would help confirm that this material is indeed organic and does not consist of precipitated inorganic salts.

TABLE 3

Recovery of monomeric sugars from hydrolyzed, dry pellets expressed as a percentage of total material recovered. Hydrolysis was tested with 3 acid concentrations; in each case hydrolysis was carried out for 1 hour in the autoclave at a temperature of 121° C.

| Hydrolysis condition | Glucose | Xylose | Galactose | Arabinose | Mannose | Total quantified |
|---|---|---|---|---|---|---|
| 3% H2SO4 | 5.80% | 7.16% | 7.10% | 7.33% | 4.30% | 31.70% |
| 1.5% H2SO4 | 5.78% | 9.28% | 3.91% | 8.72% | 2.87% | 30.56% |
| 0.5% H2SO4 | 3.50% | 5.54% | 2.03% | 5.83% | 1.45% | 18.36% |

C. Fermentation of Cyanobacterial Sugars at Shake Flask Scale

Following the development of recovery and analytical protocols, the process was scaled to a larger 0.1 m² Millipore TFF membrane to produce quantities of polysaccharide sufficient for fermentation baselining at shake flask scale. Approximately 20 L of fresh cyanobacterial supernatant was processed and hydrolyzed directly with no intermediate ethanol precipitation. The resulting hydrolysates were evaluated as a fermentation feedstock alongside pure glucose and negative controls (Table 4). The oleaginous yeast *Rhodosporidium toruloides* was used as a test organism; this strain was chosen due to its flexible metabolism and known tolerance for hydrolysis byproducts.

TABLE 4

Hydrolysis conditions and final optical density for fermentation baselining with R. toruloides. Acid hydrolysis was carried out for 1 hour at 121° C. Enzymatic hydrolysis was carried out for 24 hours at 50° C.

| Hydrolysis method | Treatment | Glucose (g/L) | Fermentation final $OD_{600}$ |
|---|---|---|---|
| None | Glucose only control | 1.0 g/L | 0.73 |
| None | No carbon control | 0 g/L | 0.08 |
| None | Cyanobacterial culture supernatant | 0.25 g/L | 0 |
| None | Concentrated polysaccharide | 0 g/L | 0.14 |
| Acid | 0.1% Sulfuric acid | 0.15 g/L | 0.84 |
| Acid | 0.3% Sulfuric acid | 0.16 g/L | 0.72 |
| Acid | 1.0% Sulfuric acid | 0.51 g/L | 0.73 |
| Acid | 3.0% Sulfuric acid | 0.7 g/L | 0.85 |
| Enzymatic | Enzyme only - no polysaccharide | 1.15 g/L | 0.64 |
| Enzymatic | 20 mg CTEC2/g solids | 0 g/L | NA |
| Enzymatic | 64 mg CTEC2/g solids | 0.92 g/L | 1.07 |
| Enzymatic | 200 mg CTEC2/g solids | 2.19 g/L | NA |

Fermentation results were promising, particularly for dilute acid conditions, with final optical density per g glucose higher than the glucose-only control. While high concentrations of acid (above 1%) are necessary to achieve complete saccharification, concentrations as low as 0.1% achieved the same final OD, indicating that even incomplete saccharification is sufficient to achieve complete metabolism of available glucose. Enzymatic saccharification was less promising both in terms of saccharification and fermentation; this is likely due to use of enzymes tailored for cellulose and hemicellulose, as opposed to cyanobacterial polysaccharides with complex monomeric composition and unknown bonding characteristics. Ultimately, due to the low glucose content of the raw polysaccharide, use of this material as a fermentation medium will be contingent upon cultivation of organisms with high metabolic flexibility.

EXAMPLE 2

Objective: Test gel formation using a monovalent and a divalent base.

Methods and Materials: Concentrated polysaccharides (13×) from Pond 3 (EPS). Raw broth is processed by Alfa-Laval disc stack centrifuge with incomplete biomass removal. Light phase is a light brown with residual biomass. Material is then concentrated by 0.5 m² 10 kd V-type Millipore Tangential Flow Filtration (TFF), resulting in a darker brown material with polysaccharides, biomass (cyanobacteria and heterotrophic bacterial contaminants) and presumably cell debris.

Bases: 5N Ammonium hydroxide ($NH_4OH$); 0.04 M (saturated) Calcium hydroxide ($Ca(OH)_2$)

$NH_4OH$:
1. 5 ml aliquots of EPS are added to 2, 15 ml tubes.
2. 1 ml $NH_4OH$ is added to each tube and mixed by hand.
3. Tubes are centrifuged for 10 min. 3,220×g.
4. Supernatant is decanted.

$Ca(OH)_2$:
1. 1 ml aliquots of EPS are added to 2, 15 ml tubes.
2. 5 ml $Ca(OH)_2$ is added to each tube and mixed by hand.
3. Tubes are centrifuged for 10 min. 3,220×g.
4. Supernatant is decanted.

Results and Conclusions: The $NH_4OH$ supernatant is clear and colorless. The gel formed immediately upon addition of the base and is a solid brown block at the bottom of the tube after centrifugation. The $Ca(OH)_2$ supernatant is clear and colorless. The gel forms immediately upon addition of the base and is a solid brown block at the bottom of the tube after centrifugation. Mono and divalent base are equally effective at forming a solid gel. Biomass remains in the gel fraction resulting in a colored gel. Residual biomass in the gel may impact performance and product acceptance. Commerical applications will benefit from selection of the least expensive base.

EXAMPLE 3

Objective: Test gel formation using monovalent and divalent bases. Residual biomass is removed prior to gel formation. Dafiltered EPS from different ponds and different residual salt concentrations are tested.

Methods and Materials: Concentrated polysaccharides (10×) from Pond 3 and Pond 1 (EPS) are used. Raw broth (Pond 3) is processed by Alfa-Laval disc stack centrifuge with incomplete biomass removal. Light phase is a light brown with residual biomass. Material is then concentrated 10× by Millipore Tangential Flow Filtration, resulting in a darker brown material with polysaccharides, biomass (cyanobacteria and heterotrophic bacterial contaminants) and presumably cell debris. An aliquot of the concentrated polysaccharide is previously diafiltered using Millipore Tangential Flow Filtration and reverse osmosis distilled water to a final conductivity of 1.72 mS/cm. 2×50 ml aliquots of material are Centrifuged 20 min at 3,220 rcf. After base addition tubes are well mixed by hand then centrifuged for 10 min. at 3,220 rcf. Raw broth (Pond 1) is centrifuged in 50 ml tubes at 3220 rcf resulting in a very light tan colored light phase. The EPS is concentrated (12.5×) and diafiltered on a Millipore 0.05 m² 100 kD V screen TFF to a final conductivity of 5.34 mS/cm. An aliquot is further diafiltered to a final conductivity of 952 µS/cm.

Bases: 5N Ammonium hydroxide (NH$_4$OH); 0.04 M (saturated) Calcium hydroxide (Ca(OH)$_2$); 13.4 M Potassium hydroxide (KOH)

TABLE 5

Multiple base gel formation - Pond 3 EPS.

| Base | Base (ml) | EPS (ml) (10 × Conc/Dia) 1.72 mS/cm | Gel Formation Notes |
|---|---|---|---|
| 5N NH$_4$OH | 5.0 | 1.0 | Rapid but incomplete gel formation. Semi-solid material remains in suspension. |
| | +2.0 | — | Incomplete gelling, semi-solid material remains in suspension. |
| | +3.0 | — | No additional gel, no solid pellet. |
| 13.4M KOH | 5.0 | 1.0 | Rapid but incomplete gel formation. Semi-solid material remains in suspension. |
| | +2.0 | — | Incomplete gelling, no solid pellet |
| | +3.0 | — | No additional gel, no solid pellet. |
| Sat. Ca(OH)$_2$ | 1.0 | 5.0 | Rapid, complete gel formation. Solid pellet after centrifugation. |

(note: each condition run in duplicate with same results. +indicates additional base added to same tubes.)

TABLE 6

Multiple base gel formation - Pond 1 EPS.

| Base | ml Base | EPS (ml) (10 × Conc/Dia) 5.34 mS/cm | Gel Formation Notes |
|---|---|---|---|
| 5N NH$_4$OH | 1.0 | 1.0 | Rapid, complete gel formation. Semi-solid brownish pellet after centrifugation. |
| 13.4M KOH | 1.0 | 1.0 | Rapid, complete gel formation. Semi-solid brownish pellet after centrifugation. |
| Sat. Ca(OH)$_2$ | 1.0 | 5.0 | Incomplete gel formation, semi-solid pellet after centrifugation. |
| | +2.0 | — | Complete gel fromation. Solid brownish pellet after centrifugation. |

Results and Conclusions: Centrifugation of the concentrated, diafiltered EPS results in a small green pellet but most of the residual biomass remained in the supernatant. Viscosity of the concentrated material precludes residual biomass removal. Cell-free material needs to be derived from the dilute EPS. Non-diafiltered concenterated EPS forms a more solid pellet than diafiltered EPS. Diafiltered EPS with more residual salt forms a more solid gel than the lowest conductivity EPS (which essentially do not form a gel), indicating that salt in the EPS plays some role in gel formation. Ca(OH)$_2$ produces a more solid pellet than either NH$_4$OH or KOH, for both diafiltered samples, indicating that divalent bases improve gel formation at lower salt concentrations. At higher salt concentrations mono- and di-valent bases are equally effective in gel formation.

EXAMPLE 4

Objective: Test gel formation using NaOH and Ca(OH)$_2$ on nondiafiltered EPS. Test straining gel through cheesecloth vs. centrifugation.

Materials and Methods: Concentrated polysaccharides (10×) from Pond 3 (EPS). Raw broth is processed by Alfa-Laval disc stack centrifuge with incomplete biomass removal. Light phase is a light brown with residual biomass. The material is then concentrated by Millipore Tangential Flow Filtration, resulting in a darker brown material with polysaccharides, biomass (cyanobacteria and heterotrophic bacterial contaminants) and presumably cell debris.

Bases: 10 N Sodium hydroxide (NaOH); 0.04 M (saturated) Calcium hydroxide (Ca(OH)$_2$).

TABLE 7

Multiple base gel formation - Pond 3 EPS.

| Base | Base (ml) | EPS (ml) (10 × Conc) | Gel Formation Notes |
|---|---|---|---|
| 10N NaOH | 5.0 | 20.0 | Rapid but incomplete gel formation. Semi-solid material remains in suspension. |
| | +5.0 | — | No additional gel, no solid pellet. |
| Sat. Ca(OH)$_2$ | 10.0 | 20.0 | Rapid, complete gel formation. Solid pellet after centrifugation. Clear supernatant, decanting loses semi-solid gel. |
| | +20.0 | — | More complete gel formation, solid brownish pellet, clear supernatant easily decanted. |

(note: each condition run in duplicate with same results. +indicates additional base added to same tubes.)

Results and Conclusions: Ca(OH)$_2$ at 1:1 with concentrated EPS forms a solid pellet that is easily separated from the supernatant. NaOH forms a less solid pellet that does not separate via centrifugation. Straining gelled material through cheesecloth results in a semi-solid materials, especially for the NaOH. Capturing EPS via base gellation is more efficient with Ca(OH)$_2$ but still requires additional processing via centrifugation or straining. Calcium hydroxide is commonly used in water treatment and food processing, has low toxicity, is relatively easy to handle and has a relatively low cost ($100-150/MT). Sodium hydroxide is used to manufacture soaps, paper, petroleum products, is highly corrosive and has a higher cost (>$300/MT). Potassium hydroxide is widely used including as a food thickener or stabilizer, is highly corrosive and has a higher cost (>$200/MT). Ammonium hydroxide is used in the manufacture of products such as fertilizer, plastic, rayon and rubber. It is irritating to the eyes and has toxicological properties, and a moderate cost (>$160/MT). Given these considerations calcium hydroxide is recommended for commercial applications.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of producing a polysaccharide gel comprising: (a) culturing or growing a cyanobacterium or a mixture of cyanobacteria species in a medium under conditions such that the cyanobacterium or the mixture of cyanobacteria species produces a polysaccharide or a mixture of polysaccharides, (b) optionally separating the polysaccharide or the mixture of polysaccharides from the medium and/or the cyanobacterium or the mixture of cyanobacteria species, and (c) increasing the pH of the polysaccharide or the mixture of polysaccharides such that the polysaccharide or the mixture of polysaccharides forms a gel.

2. The method of claim 1, wherein the (c) increasing the pH of the polysaccharide or the mixture of polysaccharides step comprises introducing a base to the polysaccharide or the mixture of polysaccharides.

3. The method of claim 2, wherein the base is a monovalent base or a divalent base, or a mixture thereof.

4. The method of claim 3, wherein the monovalent base is ammonium hydroxide, sodium hydroxide or potassium hydroxide, or a mixture thereof.

5. The method of claim 3, wherein the divalent base is calcium hydroxide.

* * * * *